United States Patent [19]

Dong

[11] Patent Number: 5,282,865
[45] Date of Patent: Feb. 1, 1994

[54] HUMERAL SHOULDER PROSTHESIS
[75] Inventor: Nicholas N. G. Dong, Little Falls, N.J.
[73] Assignee: Osteonics Corp., Allendale, N.J.
[21] Appl. No.: 903,068
[22] Filed: Jun. 22, 1992
[51] Int. Cl.⁵ .............................................. A61F 2/40
[52] U.S. Cl. ......................................................... 623/19
[58] Field of Search .................. 623/16, 18, 19, 20, 623/22, 23

[56] References Cited

U.S. PATENT DOCUMENTS

| | | | |
|---|---|---|---|
| 2,719,522 | 10/1955 | Hudack | 623/23 |
| 2,765,787 | 11/1956 | Pellet | 623/19 |
| 3,694,820 | 10/1972 | Scales et al. | 623/19 |
| 3,803,641 | 4/1974 | Golyakhovsky | 623/19 |
| 3,842,442 | 10/1974 | Kolbel | 623/19 |
| 3,869,730 | 3/1975 | Skobel | 623/19 |
| 3,891,998 | 7/1975 | Lennox | 623/19 |
| 3,916,451 | 11/1975 | Buechel et al. | 623/19 |
| 3,978,528 | 9/1976 | Crep | 623/19 |
| 3,979,778 | 9/1976 | Stroot | 623/19 |
| 4,003,095 | 1/1977 | Gristina | 623/19 |
| 4,030,143 | 6/1977 | Elloy et al. | 623/19 |
| 4,040,131 | 8/1977 | Gristina | 623/19 |
| 4,045,825 | 9/1977 | Stroot | 623/19 |
| 4,045,826 | 9/1977 | Stroot | 623/19 |
| 4,051,559 | 10/1977 | Pifferi | 623/22 |
| 4,054,955 | 10/1977 | Seppo | 623/19 |
| 4,179,758 | 12/1979 | Gristina | 623/19 |
| 4,206,517 | 6/1980 | Pappas et al. | 623/19 |
| 4,261,062 | 4/1981 | Amstutz et al. | 623/19 |
| 4,279,041 | 7/1981 | Buchholz | 623/19 |
| 4,355,427 | 10/1982 | Schneider | 623/19 |
| 4,524,467 | 6/1985 | DeCarlo, Jr. | 623/19 |
| 4,532,661 | 8/1985 | Halpern | 623/23 |
| 4,546,501 | 10/1985 | Gustilo et al. | 623/23 |
| 4,693,723 | 9/1987 | Gabard | 623/19 |
| 4,865,605 | 9/1989 | Dines et al. | 623/19 |
| 4,919,669 | 4/1990 | Lannelongue | 623/19 |
| 4,919,670 | 4/1990 | Dale et al. | 623/19 |
| 4,964,865 | 10/1990 | Burkhead et al. | 623/19 |
| 4,986,833 | 1/1991 | Worland | 623/19 |
| 5,032,132 | 7/1991 | Matsen, III et al. | 623/19 |

FOREIGN PATENT DOCUMENTS

| | | | |
|---|---|---|---|
| 0201407 | 11/1986 | European Pat. Off. | 623/23 |
| 0339530 | 11/1989 | European Pat. Off. | 623/23 |
| 3600804 | 8/1987 | Fed. Rep. of Germany | 623/23 |
| 2579454 | 10/1986 | France | 623/19 |
| 9118559 | 12/1991 | PCT Int'l Appl. | 623/23 |

OTHER PUBLICATIONS

"Bio-Modular Total Shoulder", undated 2-page advertisement, Biomet Inc.
Bio-Modular Total Shoulder Surgical Technique, 13-page booklet, undated, Biomet Inc.
Buechel-Pappas Total Shoulder System, undated 2-page brochure, Endotec.
Fenlin Total Shoulder, undated 3-page brochure.
"Shouldering the Responsibility", undated advertisement—DePuy, Inc.

*Primary Examiner*—David Isabella
*Attorney, Agent, or Firm*—Samuelson & Jacob

[57] ABSTRACT

A modular humeral shoulder prosthesis for implant in a predetermined position in the natural humerus to replace the natural humeral head of a shoulder joint with a prosthetic implant has a humeral head component including a humeral head member with a spherical bearing surface of predetermined radius extending from an origin to the bearing surface, an undersurface extending in a first direction, an elongate post integral with and projecting in a given direction from the humeral head member, the given direction making a first acute angle with the first direction, and a post portion on the post, and a humeral stem component including a platform having an upper surface, a stem integral with and depending from the platform, the stem extending along a longitudinal axis for alignment generally longitudinally along the natural humerus, the upper surface extending in a second direction making a second acute angle with the longitudinal axis, and an elongate recess in the stem, the recess extending along the stem and including at least a recess portion complementary to the post portion for reception of the post portion within the recess portion in an integrated coupled assembly wherein the humeral head component is affixed to the humeral stem component with the undersurface of the humeral head member confronting the upper surface of the platform when the bearing surface is in the predetermined position to replace the natural humeral head.

12 Claims, 2 Drawing Sheets

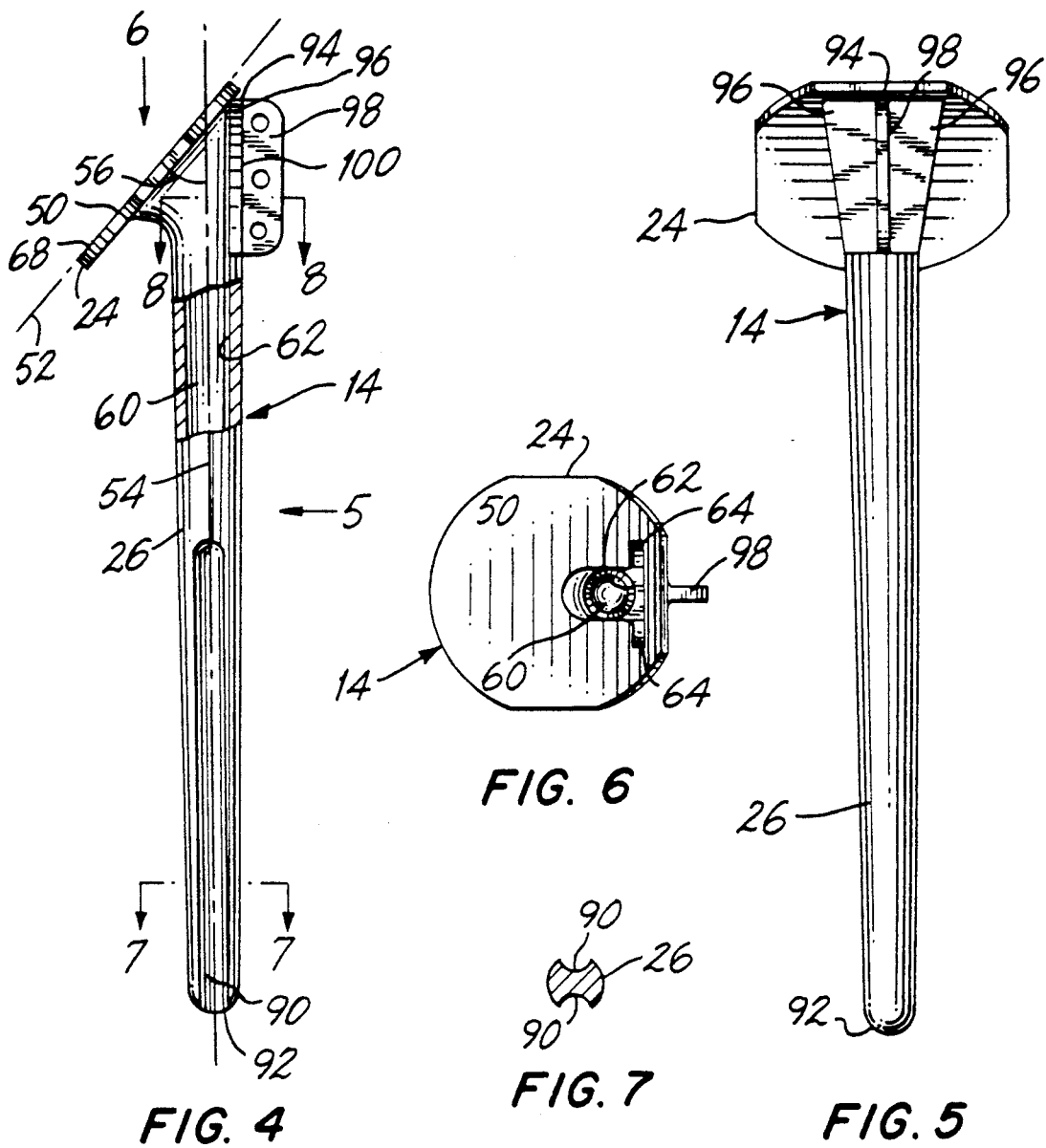

HUMERAL SHOULDER PROSTHESIS

The present invention relates generally to prosthetic implants and pertains, more specifically, to a humeral shoulder prosthesis for implant in the natural humerus to replace the natural humeral head of a shoulder joint with a prosthetic implant.

It has been suggested that a humeral prosthesis of a prosthetic shoulder implant can be constructed in a modular fashion in which the humeral head is included in a humeral head component selectively coupled, as by an interconnecting taper arrangement, with a humeral stem component. The advantages of such modular construction are described in U.S. Pat. No. 4,865,605.

The present invention attains the advantages of modular construction in a humeral shoulder prosthesis, and includes improvements which exhibit several additional objects and advantages, some of which are summarized as follows: Facilitates the construction and implant of a prosthetic humeral head having the requisite larger diameter with a relatively reduced head height for more accurate replacement of the natural humeral head; utilizes the natural humeral canal to greater advantage in accommodating the implant and managing the forces placed on the implant during use; enables options which tend to reduce the trauma normally associated with the implant procedure; attains greater stability upon implant in the natural humerus; provides a wider range of choices to the surgeon in accommodating the various conditions encountered at the implant site in different recipients of a humeral shoulder prosthesis; simplifies the implant procedure while enabling greater accuracy in effecting the implant; exhibits exemplary performance over a relatively long service life.

The above objects and advantages, as well as further objects and advantages, are attained by the present invention which may be described briefly as a modular humeral shoulder prosthesis for implant in a predetermined position in the natural humerus to replace the natural humeral head of a shoulder joint with a prosthetic implant, the humeral shoulder prosthesis comprising: a humeral head component including a humeral head member having a spherical bearing surface with a predetermined radius extending from an origin to the bearing surface, an undersurface extending in a first direction, an elongate post integral with and projecting in a given direction from the humeral head member, the given direction making a first acute angle with the first direction, and a post portion on the post; and a humeral stem component including a platform having an upper surface a stem integral with and depending from the platform, the stem extending along a longitudinal axis for alignment generally longitudinally along the natural humerus, the upper surface extending in a second direction making a second acute angle with the longitudinal axis, and an elongate recess in the stem, the recess extending along the stem and including at least a recess portion complementary to the post portion for reception of the post portion within the recess portion in an integrated coupled assembly wherein the humeral head component is affixed to the humeral stem component with the undersurface of the humeral head member confronting the upper surface of the platform when the bearing surface is in the predetermined position to replace the natural humeral head. In addition, the invention contemplates use of the humeral head component as an implant independent of the humeral stem component.

The invention will be understood more fully, while still further objects and advantages will become apparent, in the following detailed description of preferred embodiments of the invention illustrated in the accompanying drawing, in which:

FIG. 4 is a front elevational view of a humeral stem component of the prosthesis;

FIG. 5 is a side elevational view of the humeral stem component, taken in the direction of arrow 5 in FIG. 4;

FIG. 6 is top plan view of the humeral stem component taken in the direction of the arrow 6 in FIG. 4;

FIG. 7 is a cross-sectional view taken along line 7—7 of FIG. 4;

FIG. 8 is a fragmentary cross-sectional view taken along line 8—8 of FIG. 4; and FIG. 9 is a fragmentary cross-sectional view similar to FIG. 8, but showing an alternate construction for the humeral stem component.

Figure 1:
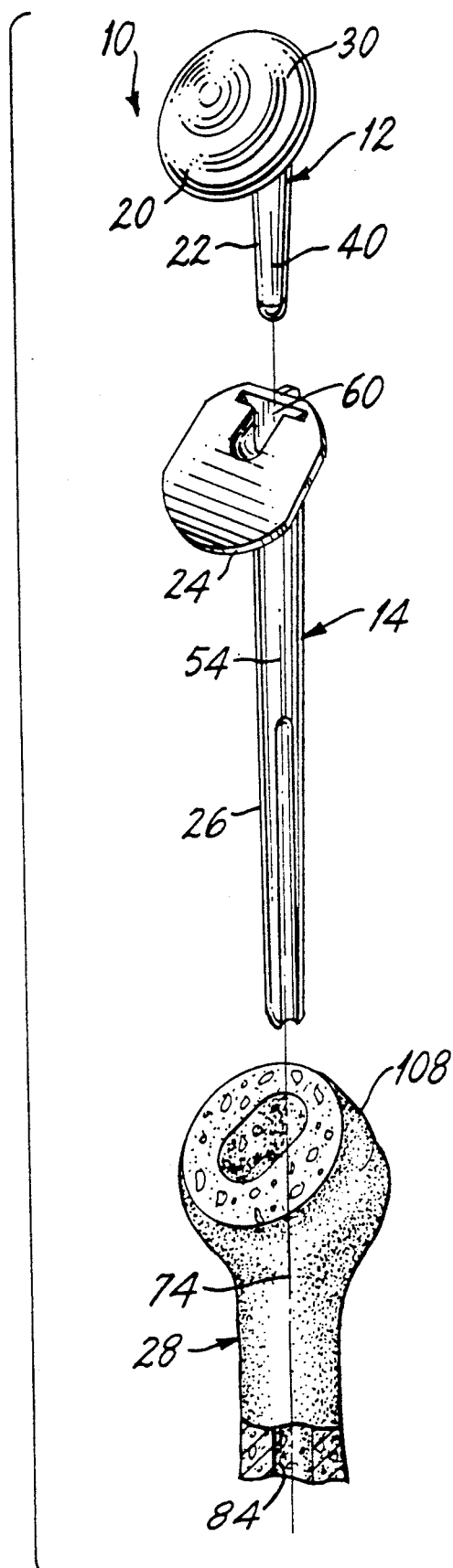
FIG. 1 is an exploded perspective view of a modular humeral shoulder prosthesis constructed in accordance with the present invention, at an implant site.

Referring now to the drawing, and especially to FIG. 1 thereof, a modular humeral shoulder prosthesis constructed in accordance with the present invention is shown generally at 10 and is seen to have a humeral head component 12 and a humeral stem component 14. Humeral head component 12 includes a humeral head member 20 and an elongate post 22 integral with and depending from the head member 20 to project downwardly toward the stem component 14. In the preferred construction, humeral head component is in the form of a unitary structure constructed of a known bio-compatible material, such as a cobalt-chrome alloy. Humeral stem component 14 includes a proximal platform 24 and an elongate stem 26 integral with and depending from the platform 24 to project downwardly for reception in a suitably prepared natural humerus 28, in a predetermined position in the humerus 28. In the preferred construction, humeral stem component 14 is in the form of a unitary structure constructed of a known bio-compatible material, such as titanium or a cobalt-chrome alloy.

Figure 2:
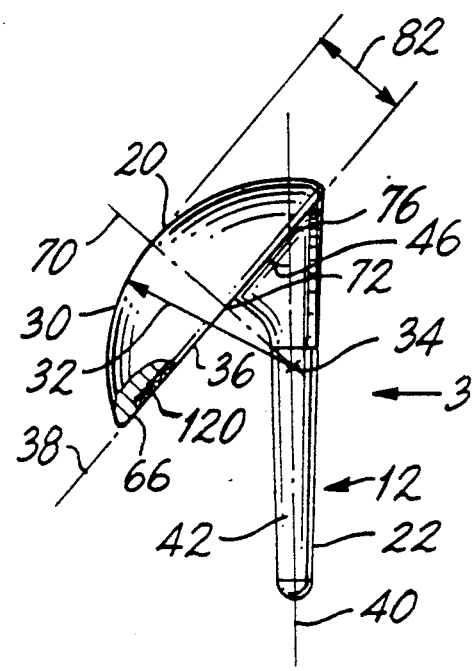
FIG. 2 is a front elevational view of the humeral head component of the prosthesis.
Figure 3:
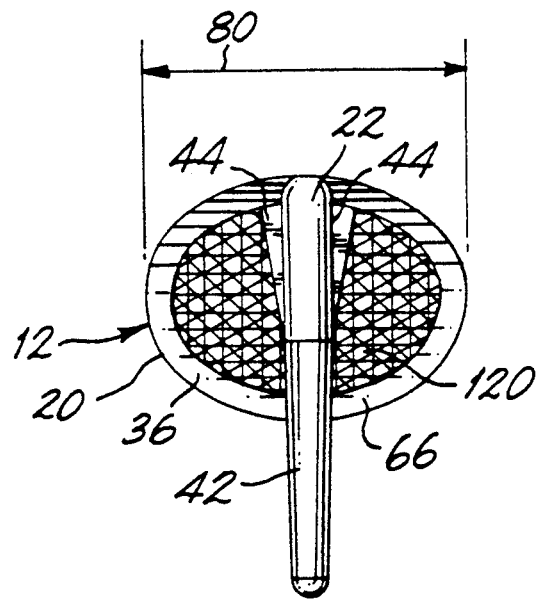
FIG. 3 is a side elevational view of the humeral head component, taken in the direction of arrow 3 in FIG. 2.

Turning now to FIGS. 2 and 3, as well as to FIG. 1, the humeral head member 20 of humeral head component 12 is in the form of a generally spherical segment having a single base and includes a bearing surface 30, which follows a spherical surface contour having a predetermined radius 32 extending from an origin 34, and an undersurface 36, which extends along the base of the spherical segment in a direction lying in chordal plane 38. The post 22 projects downwardly, in a given direction along a central axis 40, and includes a post portion 42 for coupling the post 22 with the humeral stem component 14, as set forth below. Reinforcing webs 44 extend in anterior-posterior directions between the post 22 and the head member 20, at the proximal end of the post 22 where the post 22 joins the head member 20, to reinforce the integration of the post 22 with the head member 20. The central axis 40 makes an acute angle 46 with the chordal plane 38.

As best seen in FIGS. 4 through 6, as well as in FIG. 1, the platform 24 of the humeral stem component 14 includes an upper surface 50 which extends in a direction lying in a plane 52 and a lower surface 53 generally parallel to upper surface 50. The stem 26 extends downwardly along a longitudinal axis 54, and the plane 52 makes an acute angle 56 with the longitudinal axis 54. An elongate recess 60 extends into the stem 26, along the longitudinal axis 54, and includes a recess portion 62 complementary with the post portion 42 for reception of the post portion 42 within the recess portion 62 in an integrated coupled assembly wherein the humeral head component 12 is affixed to the humeral stem component 14 for use. In the preferred construction, the post portion 42 and the complementary recess portion 62 follow a Morse taper which serves to lock the post 22 within the stem 26 upon appropriate joining of the humeral head component 12 and the humeral stem component 14. Recess 60 includes further portions 64 complementary with the webs 44 of the humeral head component 12 to enable appropriate engagement of the head component 12 with the stem component 14.

In the preferred construction, upper surface 50 of the platform 24 of the humeral stem component 14 is generally flat and lies essentially within plane 52. In order to assure that the head member 20 is seated properly and confronts the platform 24 when the head component 12 is joined with the stem component 14, the undersurface 36 includes at least an undersurface portion in the form of a basal surface 66 extending adjacent the outer periphery of the undersurface 36. Basal surface 66 is essentially planar and lies in the chordal plane 38. Upper surface 50 of the platform 24 includes a complementary surface 68 lying in plane 52 for confrontation with basal surface 66 when the head component 12 is joined with the stem component 14.

As best seen in FIG. 2, humeral head member 20 includes a central axis 70 which is normal to the chordal plane 38 at a central portion 72 of the undersurface 36 and passe through the origin 34 of radius 32 of the spherical surface contour of the bearing surface 30. In the preferred construction, the origin 34 lies within the post 22 and preferably is located on the central axis 40 of the post 22. In order to better accommodate the forces applied to the humeral head member 20 during service, the humeral head member 20 is offset from the post 22, and the acute angle 46 between the chordal plane 38 and the central axis 40 of the post 22 is such that the post 22 is aligned with the longitudinal axis 74 of the natural humerus 28 when the humeral head component 12 is joined with the humeral stem component 14 and the stem component 14 is implanted in the humerus 28. Thus, the intersection of the central axis 70 of the humeral head member 20 with the chordal plane 38, at central portion 72, is spaced laterally from the central axis 40 of the post 22, and the post 22 is joined with the humeral head member 20 along the undersurface 38 at a location 76 spaced from the central portion 72. That arrangement enables the required larger spherical segment base diameter 80 of the humeral head member 20, and a reduced height 82, while accommodating the desired alignment of the central axis 40 of the post 22 with the longitudinal axis 54 of the stem 26, without excessive offset of the bearing surface 30 from the longitudinal axis 54 of the stem 26. Since the highest forces applied to the prosthesis 10 during use generally are aligned with the longitudinal humeral axis 74, the alignment of the longitudinal axis 54 of the stem 26 of the stem component 14 with the longitudinal humeral axis 74 and the alignment of the central axis 40 of the post 22 with the longitudinal axis 54 of the stem 26 enables increased stability in the implant. By following the longitudinal humeral axis 74, the prosthesis 10 utilizes the humeral canal 84 to better advantage in managing the stresses encountered during service. Alignment of the central axis 40 of the post 22 with the humeral axis 74 enables the employment of a relatively long post 22 and enhances the engagement between the humeral head component 12 and the humeral stem component 14 and the maintenance of that engagement during service. In order to accomplish the desired alignment, as set forth above, over a range of sizes of prosthesis 10, the acute angles 46 and 56 preferably are about forty degrees.

Upon implant, the stem 26 of the humeral stem component 14 extends into the humeral canal 84 and the platform 24 is seated upon the natural humerus 28 with the lower surface 53 confronting the prepared natural humerus 28. In order to increase the rotational stability of the stem 26 in the humeral canal 84, longitudinal grooves 90 are provided in the stem 26 adjacent the distal end 92 of the stem 26. As illustrated in FIG. 7, the grooves 90 are diametrically opposite one another in the distal portion of the stem 26. In addition to increasing the rotational stability of the implanted stem 26, the grooves 90 have a longitudinal extent sufficient to provide channels for the relief of cement which can flow in the grooves 90 during a cemented implant of the humeral stem component 14.

Referring now to FIG. 8, as well as to FIGS. 4 and 5, rotational stability is enhanced at the proximal end 94 of the humeral stem component 14 by flanges 96 and 98 integral with the stem component 14 adjacent the proximal end 94 of the stem component 14 and extending outwardly from the laterally outer surface 100 of the stem component 14. Flanges 96 are aligned with the anterior-posterior direction, while flange 98 extends generally perpendicular to the flanges 96, in the medial-lateral direction. In the embodiment illustrated in FIG. 9, such rotational stability is provided by an alternate arrangement in which flanges 102, while essentially perpendicular to one another in a V-shaped array, are oriented so that each of the flanges 102 extends outwardly from the laterally outer surface 100 in a direction lying between the anterior-posterior and medial-lateral directions. In this manner, the flanges 102 will follow more closely the greater tubercle 104 and the lesser tubercle 106 of the proximal humerus 108 for better seating within the bone of the natural humerus. In addition, the V-shaped array enables the accommodation of some interoperative adjustments in retroversion by enabling rotational adjustments of the humeral stem component 14 relative to the natural humerus 28 without the flanges 102 entering the intertubercular groove 110 between the greater and lesser tubercles 104 and 106 of the proximal humerus 108.

Returning now to FIGS. 2 and 3, the alignment of the post 22 of the humeral head component 12 along the central axis 40 which is made to follow the humeral axis 74, together with the increased longitudinal extent of the post 22 permitted by such an orientation of the post 22 relative to the head member 20, enables the use of the humeral head component 12 as an implant independent of the humeral stem component 14. Thus, where it is determined that conditions at the implant site do not require the utilization of a humeral stem component 14, the humeral head component 12 may be implanted directly in the natural humerus 28 as a replacement for the natural humeral head. In such an instance, the post 22 serves as a stem for securing the implant in the natural humerus. The longitudinal extent of the post 22 enables appropriate seating of the humeral head component 12 at the proximal humerus 108. To this end, the undersurface 38 is provided with a further surface portion 120 having a surface treatment, such as a knurled pattern, which will encourage the ingrowth of bone for affixation of the humeral head component 12 directly to the natural humerus. Such surface treatments are well known in the art of prosthetic implants. Further surface portion 120 is recessed somewhat from the basal surface 66 so as not to interfere with the appropriate confrontation of the basal surface 66 with the complementary surface 68 of the upper surface 50 of the platform 24 of the humeral stem component 14 when the humeral head component 12 is utilized in connection with a stem component 14. The ability to use the humeral head component 12 without the humeral stem component 14 at an implant site enables the replacement of the natural humeral head with minimal trauma, where conditions at the implant site permit such use.

It will be seen that the present invention attains the objects and advantages summarized above, namely: Facilitates the construction and implant of a prosthetic humeral head having the requisite larger diameter with a relatively reduced head height for more accurate replacement of the natural humeral head; utilizes the natural humeral canal to greater advantage in accommodating the implant and managing the forces placed on the implant during use; enables options which tend to reduce the trauma normally associated with the implant procedure; attains greater stability upon implant in the natural humerus; provides a wider range of choices to the surgeon in accommodating the various conditions encountered at the implant site in different recipients of a humeral shoulder prosthesis; simplifies the implant procedure while enabling greater accuracy in effecting the implant; exhibits exemplary performance over a relatively long service life.

It is to be understood that the above detailed description of preferred embodiments of the invention are provided by way of example only. Various details of design and construction may be modified without departing from the true spirit and scope of the invention as set forth in the appended claims.

The embodiments of the invention in which an exclusive property or privilege is claimed are defined as follows:

1. A modular humeral shoulder prosthesis for implant in a predetermined position in the natural humerus to replace the natural humeral head of a shoulder joint with a prosthetic implant, the humeral shoulder prosthesis comprising:

a humeral head component including a humeral head member having a spherical bearing surface with a predetermined radius extending from an origin to the bearing surface, an undersurface extending in a first direction and including a central location, an elongate post integral with and projecting in a given direction from the humeral head member, the given direction making a first acute angle with the first direction, the post extending along an axis which intersects the undersurface at a further location spaced laterally away from the central location, the post being integral with the humeral head member at said further location, and a post portion on the post; and a humeral stem component including a platform having an upper surface, a stem integral with and depending from the platform, the stem extending along a longitudinal axis for alignment generally longitudinally along the natural humerus, the upper surface extending in a second direction making a second acute angle with the longitudinal axis, and an elongate recess in the stem, the recess extending along the stem and including at least a recess portion complementary to the post portion for reception of the post portion within the recess portion in an integrated coupled assembly wherein the humeral head component is affixed to the humeral stem component with the undersurface of the humeral head member confronting the upper surface of the platform when the bearing surface is in the predetermined position to replace the natural humeral head.

2. The invention of claim 1 wherein the humeral head member is in the form of a generally spherical segment having a basal surface lying essentially in a chordal plane, the chordal plane being spaced radially away from the origin of the radius of the bearing surface, and the first direction lies essentially in the chordal plane.

3. The invention of claim 2 wherein the first acute angle and the second acute angle are essentially the same.

4. The invention of claim 3 wherein the first acute angle and the second acute angle each are about forty degrees.

5. The invention of claim 1 wherein the undersurface includes a central location and the post is spaced laterally away from the central location.

6. The invention of claim 1 wherein the origin of the radius of the bearing surface lies within the post.

7. The invention of claim 6 wherein the post includes a central axis and the origin of the radius of the bearing surface lies essentially on the central axis of the post.

8. The invention of claim 1 wherein the stem includes a proximal end, a distal end, and an outer surface, and at least one longitudinally extending channel in the outer surface of the stem adjacent the distal end of the stem.

9. The invention of claim 1 wherein the stem includes a proximal end, a distal end, and a laterally outer surface, and flanges extending outwardly from the laterally outer surface of the stem adjacent the proximal end of the stem, the flanges extending in a generally V-shaped array oriented such that each flange extends between anterior-posterior and medial-lateral directions.

10. The invention of claim 1 wherein the undersurface of the humeral head member of the humeral head component includes a basal surface for confronting the upper surface of the platform of the humeral stem component.

11. The invention of claim 10 wherein the undersurface has an outer periphery, and the basal surface extends along the undersurface adjacent the outer periphery of the undersurface.

12. A modular humeral shoulder prosthesis for implant in a predetermined position in the natural humerus to replace the natural humeral head of a shoulder joint with a prosthetic implant, the humeral shoulder prosthesis comprising:

a humeral head component including a humeral head member having a spherical bearing surface with a predetermined radius extending from an origin to the bearing surface, an undersurface extending in a first direction, an elongate post integral with and projecting in a given direction from the humeral head member, the given direction making a first acute angle with the first direction, the post including a central axis, the origin of the radius of the bearing surface lying within the post, essentially on the central axis of the post, and a post portion on the post; and a humeral stem component including a platform having an upper surface, a stem integral with and depending from the platform, the stem extending along a longitudinal axis for alignment generally longitudinally along the natural humerus, the upper surface extending in a second direction making a second acute angle with the longitudinal axis, and an elongate recess in the stem, the recess extending along the stem and including at least a recess portion complementary to the post portion for reception of the post portion within the recess portion in an integrated coupled assembly wherein the humeral head component is affixed to the humeral stem component with the undersurface of the humeral head member confronting the upper surface of the platform when the bearing surface is in the predetermined position to replace the natural humeral head.

* * * * *